(12) United States Patent
Kiyose

(10) Patent No.: US 10,424,719 B2
(45) Date of Patent: Sep. 24, 2019

(54) PIEZOELECTRIC MODULE, ULTRASONIC MODULE, AND ELECTRONIC APPARATUS

(71) Applicant: Seiko Epson Corporation, Tokyo (JP)

(72) Inventor: Kanechika Kiyose, Matsumoto (JP)

(73) Assignee: Seiko Epson Corporation (JP)

( * ) Notice: Subject to any disclaimer, the term of this patent is extended or adjusted under 35 U.S.C. 154(b) by 463 days.

(21) Appl. No.: 15/349,263

(22) Filed: Nov. 11, 2016

(65) Prior Publication Data

US 2017/0155028 A1 Jun. 1, 2017

(30) Foreign Application Priority Data

Nov. 30, 2015 (JP) ................................. 2015-234290

(51) Int. Cl.
*H01L 41/09* (2006.01)
*H01L 41/08* (2006.01)
(Continued)

(52) U.S. Cl.
CPC ........ *H01L 41/0825* (2013.01); *B06B 1/0622* (2013.01); *H01L 41/042* (2013.01);
(Continued)

(58) Field of Classification Search
CPC ............... H01L 41/0825; H01L 41/042; H01L 41/0474; H01L 41/0475; B61B 1/0622; A61B 8/44; A61B 8/4183; A61B 8/4494
(Continued)

(56) References Cited

U.S. PATENT DOCUMENTS

| 6,211,853 B1* | 4/2001 | Takeuchi ............... G02B 26/08 345/108 |
| 2002/0080129 A1* | 6/2002 | Takeuchi ............... G09F 9/305 345/204 |

(Continued)

FOREIGN PATENT DOCUMENTS

| JP | 2003-235098 A | 8/2003 |
| JP | 2008-118631 A | 5/2008 |

(Continued)

*Primary Examiner* — Thomas M Dougherty
(74) *Attorney, Agent, or Firm* — Harness, Dickey & Pierce, P.L.C.

(57) ABSTRACT

A piezoelectric module includes an element substrate that includes a plurality of piezoelectric bodies (piezoelectric elements) arranged in an array, and a plurality of connection electrodes (lower connection electrode and upper connection electrode) that are connected to the piezoelectric body (piezoelectric element) and are drawn between the piezoelectric body (piezoelectric element) and an adjacent piezoelectric body (piezoelectric element), an input and output circuit that is provided on one surface side of the element substrate and independently inputs and outputs a signal from and to each of the connection electrodes (lower connection electrode and upper connection electrode), and columnar electrodes (first through electrode and second through electrode) each of which is provided between each of the connection electrodes (lower connection electrode and upper connection electrode) and the input and output circuit and connects each of the connection electrodes (lower connection electrode and upper connection electrode) and the input and output circuit to each other.

10 Claims, 10 Drawing Sheets

(51) Int. Cl.
*H01L 41/04* (2006.01)
*H01L 41/047* (2006.01)
*B06B 1/06* (2006.01)
*A61B 8/00* (2006.01)

(52) U.S. Cl.
CPC ...... *H01L 41/0474* (2013.01); *H01L 41/0475* (2013.01); *A61B 8/44* (2013.01)

(58) Field of Classification Search
USPC .................................. 310/322, 334, 365
See application file for complete search history.

(56) References Cited

U.S. PATENT DOCUMENTS

| | | | |
|---|---|---|---|
| 2003/0025442 A1* | 2/2003 | Takeuchi | G02B 26/004 313/495 |
| 2003/0043449 A1* | 3/2003 | Takeuchi | G02B 26/02 359/290 |
| 2003/0102777 A1 | 6/2003 | Kuniyasu et al. | |
| 2005/0140248 A1 | 6/2005 | Kuniyasu et al. | |
| 2008/0089181 A1 | 4/2008 | Adachi et al. | |
| 2009/0034370 A1* | 2/2009 | Guo | B06B 1/0622 367/180 |
| 2010/0179430 A1 | 7/2010 | Sano et al. | |
| 2011/0071396 A1 | 3/2011 | Sano et al. | |
| 2011/0291525 A1* | 12/2011 | Maruyama | H02N 2/0015 310/334 |
| 2012/0188849 A1 | 7/2012 | Matsuda et al. | |
| 2015/0092514 A1 | 4/2015 | Kiyose et al. | |
| 2015/0288401 A1 | 10/2015 | Matsuda et al. | |

FOREIGN PATENT DOCUMENTS

| | | |
|---|---|---|
| JP | 2012-152319 A | 8/2012 |
| JP | 2015-066203 A | 4/2015 |
| WO | WO-2008-114582 A1 | 9/2008 |
| WO | WO-2009-139400 A1 | 11/2009 |

* cited by examiner

PIEZOELECTRIC MODULE, ULTRASONIC MODULE, AND ELECTRONIC APPARATUS

BACKGROUND

1. Technical Field

The present invention relates to a piezoelectric module, an ultrasonic module, and an electronic apparatus.

2. Related Art

In the related art, an ultrasonic sensor including a plurality of ultrasonic transducers mounted on a sensor substrate has been known (for example, JP-A-2012-152319).

The ultrasonic sensor disclosed in JP-A-2012-152319 mentioned above includes, for example, a matrix-like two-dimensional array structure in which four ultrasonic transducers are disposed on the sensor substrate at equal intervals along an X-axis and a Y-axis. However, such a two-dimensional array structure has a problem that wirings connected to the ultrasonic transducers become complicated.

In order to solve the above-described problem, an ultrasonic probe using a through electrode has been known (for example, Pamphlet of International Publication WO 2009/139400).

The ultrasonic probe disclosed in Pamphlet of International Publication WO 2009/139400 mentioned above includes a plurality of vibration elements each of which an electromechanical coupling coefficient or sensitivity changes depending on a bias voltage. Each of the vibration elements includes a substrate, a first film provided on the substrate, a lower electrode provided within the first film, a frame provided on the first film, a second film provided on the frame, and an upper electrode provided within the second film. In addition, the frame is provided with an opening, and an internal space (vacuum) is formed between the first film and the second film by the opening. This cMUT chip applies a pulse voltage between the lower electrode and the upper electrode to thereby vibrate the second film facing the internal space and transmit ultrasonic waves to a side opposite to the substrate.

Through holes passing through the substrate, that is, through electrodes are provided corresponding to the upper electrode and the lower electrode of the cMUT chip, and the through electrodes are connected to a signal pattern provided on a flexible substrate through the substrate. With such a configuration, the simplification of wirings is achieved.

Incidentally, in the ultrasonic probe disclosed in Pamphlet of International Publication WO 2009/139400 mentioned above, the simplification of wirings is achieved by the through electrodes, and the plurality of through electrodes are connected to a common signal pattern. Accordingly, for example, when the plurality of vibration elements are arranged lined up in one direction, appropriate power can be supplied to a vibration element disposed on a power supply side of the signal pattern, but the amount of power capable of being supplied to a vibration element decreases as the distance from the power supply side increases, which results in a problem that the vibration element cannot be driven with a high level of accuracy.

SUMMARY

An advantage of some aspects of the invention is to provide a piezoelectric module with good driving accuracy, an ultrasonic module, and an electronic apparatus.

A piezoelectric module according to an application example of the invention includes an element substrate that includes a plurality of piezoelectric bodies arranged in an array, and a plurality of connection electrodes that are connected to the piezoelectric body and are drawn between the piezoelectric body and an adjacent piezoelectric body, an input and output circuit that is provided on one surface side of the element substrate and independently inputs and outputs a signal from and to each of the connection electrodes, and columnar electrodes each of which is provided between each of the connection electrodes and the input and output circuit and connects each of the connection electrodes and the input and output circuit to each other.

In this application example, the element substrate including the plurality of connection electrodes drawn between the piezoelectric body and the adjacent piezoelectric body, among the plurality of piezoelectric bodies arranged in an array, is provided. In addition, the element substrate is provided with the columnar electrodes that are provided at positions overlapping the respective connection electrodes and connect the input and output circuit and the connection electrodes to each other.

In such a configuration, the connection electrode is drawn between the piezoelectric bodies when seen in a plan view, and the columnar electrodes are provided corresponding to the respective connection electrodes. That is, in this application example, the columnar electrodes connecting the input and output circuit and the connection electrodes of the respective piezoelectric bodies to each other are provided within an array region provided with the piezoelectric bodies arranged in an array. For this reason, for example, it is not necessary to pull around the connection electrodes to the outside of the array region (outer peripheral end of the element substrate), and thus it is possible to achieve the simplification of a wiring configuration. In addition, a terminal region for performing connection of the connection electrodes and a wiring substrate is not required to be provided at the outer peripheral end of the element substrate, and thus it is possible to achieve a reduction in the size of the element substrate.

In addition, this application example adopts a configuration in which a signal is independently input and output to each of the columnar electrodes from the input and output circuit, and thus it is possible to individually control the elements and to drive the piezoelectric bodies with a high level of accuracy.

In other words, in a configuration disclosed in JP-A-2012-152319 described above, a COM (common electrode) and an SIG (driving electrode) are common to a plurality of elements, and the plurality of elements are driven as one element group. In such a configuration, in an element distant from an input position of a signal with respect to the COM and the SIG, a voltage drop of a signal occurs, which results in deterioration in driving accuracy.

On the other hand, in this application example, since the piezoelectric bodies are independently connected to the input and output circuit through the respective columnar electrodes, the above-mentioned voltage drop of a signal does not occur, and thus it is possible to drive the piezoelectric bodies with a high level of accuracy. In addition, the piezoelectric bodies are independent of each other, and are thus allowed to function as a two-dimensional array structure. In other words, the transmission of ultrasonic waves can be controlled for each piezoelectric body, and thus it is possible to control a transmission direction of ultrasonic waves without using, for example, an acoustic lens and the like.

In the piezoelectric module according to the application example of the invention, it is preferable that the piezoelectric bodies are arranged in an array along a first direction and a second direction intersecting the first direction when seen in a plan view, and the connection electrode includes a first connection electrode which is drawn from the piezoelectric body along the first direction, and a second connection electrode which is drawn from the piezoelectric body along the second direction.

In the piezoelectric module according to the application example with this configuration, since the first connection electrode is drawn along the first direction and the second connection electrode is drawn along the second direction intersecting the first direction, and thus it is possible to densely dispose the piezoelectric bodies, as compared to a case where both the first connection electrode and the second connection electrode are drawn along the same direction (for example, only in the first direction or only in the second direction). For this reason, it is possible to reduce an array interval (distance between the adjacent piezoelectric bodies) and to promote reductions in the sizes of the element substrate and the piezoelectric module.

In the piezoelectric module according to the application example of the invention, it is preferable that the piezoelectric bodies are arranged in an array along a first direction and a second direction intersecting the first direction when seen in a plan view, the connection electrode includes a third connection electrode which is drawn to one end side of the piezoelectric body in the first direction, and a fourth connection electrode which is drawn to the other end side of the piezoelectric body in the first direction, and the third connection electrode is positioned on one end side in the second direction, and the fourth connection electrode is positioned on the other end side in the second direction.

In the piezoelectric module of the application example with this configuration, the third connection electrode is drawn to one end side of each of the piezoelectric bodies in the first direction and one end side in the second direction, and the fourth connection electrode is drawn to the other end side of each of the piezoelectric bodies in the first direction and the other end side in the second direction. For example, in a case where x- and y-axes passing through the center of each of the piezoelectric bodies are specified, the fourth connection electrode is provided on a third quadrant when the third connection electrode is provided on a first quadrant. Meanwhile, in each of the piezoelectric bodies, the fourth connection electrode may be provided on a fourth quadrant when the third connection electrode is provided on a second quadrant.

In such a configuration, a third connection electrode of one piezoelectric body and a fourth connection electrode of the other piezoelectric body in adjacent piezoelectric bodies can be disposed lined up along the second direction. For this reason, for example, it is possible to densely dispose the piezoelectric bodies in the piezoelectric module, as compared to a case where connection electrodes of adjacent piezoelectric bodies are lined up along the first direction or the second direction.

In the piezoelectric module of the application example of the invention, it is preferable that the piezoelectric bodies are arranged in an array along a first direction and a second direction intersecting the first direction when seen in a plan view, the connection electrode which is connected to a first piezoelectric body, among the plurality of piezoelectric bodies, is drawn from the piezoelectric body along the first direction, and the connection electrode which is connected to a second piezoelectric body adjacent to the first piezoelectric body is drawn from the piezoelectric body along the second direction.

In the piezoelectric module of the application example with this configuration, a drawing direction of a connection electrode of the first piezoelectric body is different from a drawing direction of a connection electrode of the second piezoelectric body. Accordingly, the connection electrode of the first piezoelectric body and the connection electrode of the second piezoelectric body are not lined up along the first direction or the second direction, and thus it is possible to densely dispose the piezoelectric bodies in the piezoelectric module.

An ultrasonic module according to an application example of the invention includes an ultrasonic transducer substrate that includes a plurality of ultrasonic transducers arranged in an array, and a plurality of connection electrodes that are connected to the ultrasonic transducer and are drawn between the ultrasonic transducer and an adjacent ultrasonic transducer, an input and output circuit that is provided on one surface side of the ultrasonic transducer substrate and independently inputs and outputs a signal from and to each of the connection electrodes, and columnar electrodes each of which is provided between each of the connection electrodes and the input and output circuit and connects each of the connection electrodes and the input and output circuit to each other.

The ultrasonic module of this application example can individually control the ultrasonic transducers and can drive the ultrasonic transducers with a high level of accuracy, similar to the above-mentioned piezoelectric module. That is, in the ultrasonic module of this application example, the columnar electrodes are provided with respect to connection electrodes of the respective ultrasonic transducers, and the columnar electrodes are connected to the input and output circuit, thereby allowing the ultrasonic transducers to be independently driven. Accordingly, the above-mentioned voltage drop of a signal does not occur, and thus it is possible to drive the ultrasonic transducers with a high level of accuracy. In addition, the ultrasonic transducers are independently provided, and are thus allowed to function as a two-dimensional array structure. In other words, the transmission of ultrasonic waves can be controlled for each ultrasonic transducer, and thus it is possible to control a transmission direction of ultrasonic waves without using, for example, an acoustic lens and the like.

In the ultrasonic module according to the application example of the invention, it is preferable that the ultrasonic transducers are arranged in an array along a first direction and a second direction intersecting the first direction when seen in a plan view, and the connection electrode includes a first connection electrode which is drawn from the ultrasonic transducer along the first direction, and a second connection electrode which is drawn from the ultrasonic transducer along the second direction.

In the ultrasonic module of the application example with this configuration, since the first connection electrode is drawn along the first direction and the second connection electrode is drawn along the second direction intersecting the first direction similar to the above-mentioned piezoelectric module, and thus it is possible to densely dispose the ultrasonic transducers in the ultrasonic module, as compared to a case where both the first connection electrode and the second connection electrode are drawn along the same direction (for example, only in the first direction or only in the second direction). For this reason, it is possible to reduce an array interval and to promote reductions in the sizes of the element substrate and the ultrasonic module.

In the ultrasonic module according to the application example of the invention, it is preferable that the ultrasonic transducers are arranged in an array along a first direction and a second direction intersecting the first direction when seen in a plan view, the connection electrode includes a third connection electrode which is drawn to one end side of the ultrasonic transducer in the first direction, and a fourth connection electrode which is drawn to the other end side of the ultrasonic transducer in the first direction, and the third connection electrode is positioned on one end side in the second direction, and the fourth connection electrode is positioned on the other end side in the second direction.

In the ultrasonic module of the application example with this configuration, the third connection electrode is drawn to one end side of each of the ultrasonic transducers in the first direction and one end side in the second direction, and the fourth connection electrode is drawn to the other end side of each of the ultrasonic transducers in the first direction and the other end side in the second direction, similar to the above-mentioned piezoelectric module. For example, in a case where x- and y-axes passing through the center of each of the ultrasonic transducers are specified, the fourth connection electrode is provided on a third quadrant when the third connection electrode is provided on a first quadrant. Meanwhile, in each of the ultrasonic transducers, the fourth connection electrode may be provided on a fourth quadrant when the third connection electrode is provided on a second quadrant.

In such a configuration, a third connection electrode of one ultrasonic transducer and a fourth connection electrode of the other ultrasonic transducer in adjacent ultrasonic transducers can be disposed lined up along the second direction. For this reason, for example, it is possible to densely dispose the ultrasonic transducers in the ultrasonic module, as compared to a case where connection electrodes of adjacent ultrasonic transducers are lined up along the first direction or the second direction.

In the ultrasonic module of the application example of the invention, it is preferable that the ultrasonic transducers are arranged in an array along a first direction and a second direction intersecting the first direction when seen in a plan view, the connection electrode which is connected to a first ultrasonic transducer, among the plurality of ultrasonic transducers, is drawn from the ultrasonic transducer along the first direction, and the connection electrode which is connected to a second ultrasonic transducer adjacent to the first ultrasonic transducer is drawn from the ultrasonic transducer along the second direction.

In the ultrasonic module of the application example with this configuration, a drawing direction of a connection electrode of the first ultrasonic transducer is different from a drawing direction of a connection electrode of the second ultrasonic transducer. Accordingly, the connection electrode of the first ultrasonic transducer and the connection electrode of the second ultrasonic transducer are not lined up along the first direction or the second direction, and thus it is possible to densely dispose the ultrasonic transducers in the ultrasonic module.

An electronic apparatus according to an application example of the invention includes a piezoelectric body substrate that includes a plurality of piezoelectric bodies arranged in an array, and a plurality of connection electrodes that are connected to the piezoelectric body and are drawn between the piezoelectric body and an adjacent piezoelectric body, columnar electrodes that are provided at positions overlapping the respective connection electrodes and pass through the piezoelectric body substrate in the thickness direction when the piezoelectric body substrate is seen from a thickness direction, an input and output circuit that independently inputs and outputs a signal from and to each of the columnar electrodes, and a control unit that controls the piezoelectric body.

In the electronic apparatus of this application example, similar to the piezoelectric module it is not necessary to pull around the connection electrodes to the outside of the array region (outer peripheral end of the element substrate), and thus it is possible to achieve the simplification of a wiring configuration. In addition, a terminal region for performing connection of the connection electrodes and a wiring substrate is not required to be provided at the outer peripheral end of the element substrate, and thus it is possible to achieve reductions in the sizes of the element substrate and the electronic apparatus, similar to the above-mentioned piezoelectric module. In addition, the above-mentioned voltage drop of a signal does not occur, and thus it is possible to drive the piezoelectric bodies with a high level of accuracy. In this manner, it is possible to perform various processes (for example, the transmission and reception of ultrasonic waves, the detection of pressure, the application of pressure, and the like) in the electronic apparatus with a high level of accuracy by driving the piezoelectric bodies with a high level of accuracy.

In the electronic apparatus of the application example of the invention, it is preferable that the control unit performs an ultrasonic wave transmission process of driving the piezoelectric body to transmit ultrasonic waves and an ultrasonic wave reception process of receiving ultrasonic waves by the piezoelectric body, and measures an object to be measured, on the basis of transmission and reception timings of the ultrasonic waves.

In the application example with this configuration, the control unit controls the piezoelectric bodies, to thereby perform ultrasonic wave transmission and reception processes and to perform measurement (measurement of ultrasonic waves) on an object to be measured, on the basis of transmission and reception timings of the ultrasonic waves. In this application example, as described above, the ultrasonic wave transmission process and the ultrasonic wave reception process in each of the piezoelectric bodies can be performed with a high level of accuracy, and thus it is possible to achieve measurement accuracy in the measurement of ultrasonic waves.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, an ultrasonic measurement apparatus as an electronic apparatus of a first embodiment according to the invention will be described with reference to the accompanying drawings.

Configuration of Ultrasonic Measurement Apparatus 1

Figure 1:
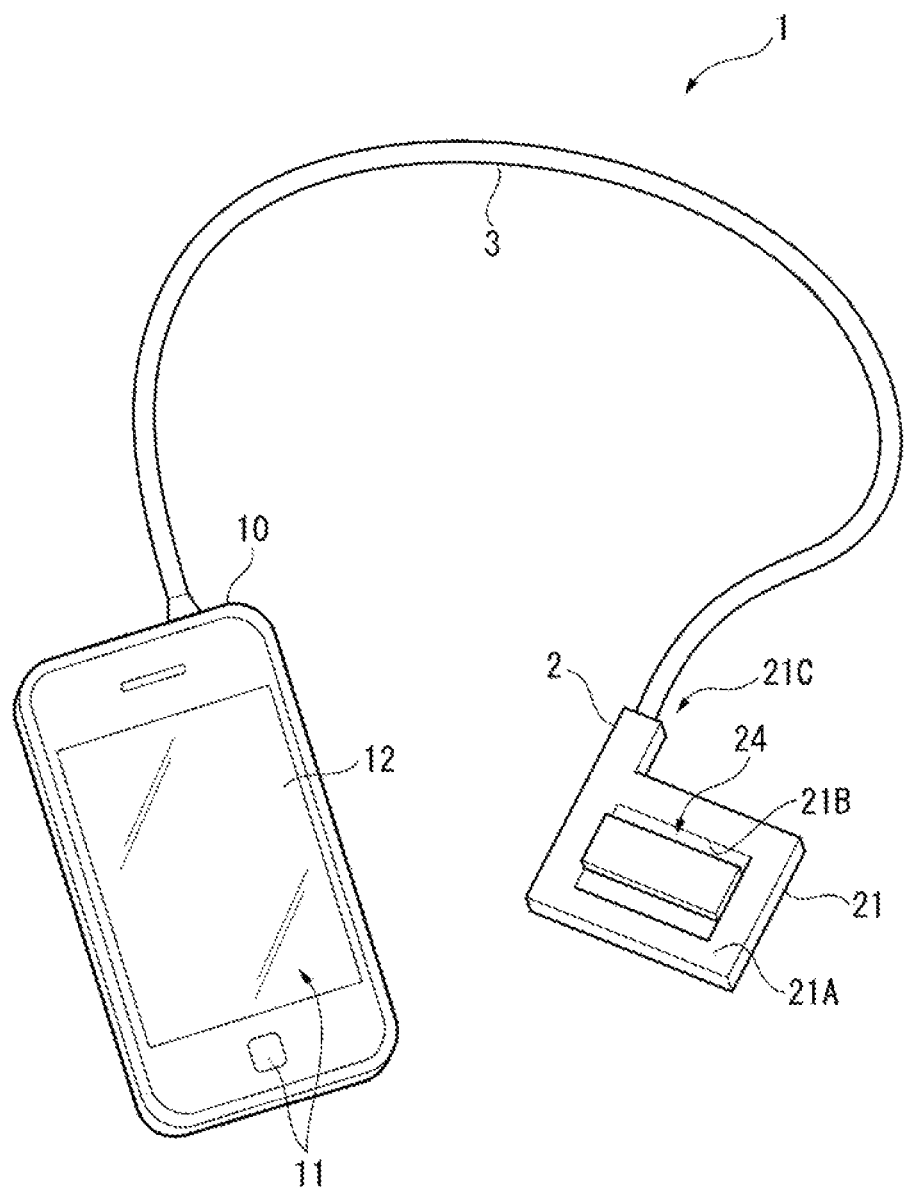
FIG. 1 is a perspective view showing a schematic configuration of an ultrasonic measurement apparatus according to a first embodiment.

FIG. 1 is a perspective view showing a schematic configuration of an ultrasonic measurement apparatus 1 according to this embodiment.

The ultrasonic measurement apparatus 1 of this embodiment includes an ultrasonic probe 2 and a control device 10 which is electrically connected to the ultrasonic probe 2 through a cable 3, as shown in FIG. 1.

The ultrasonic measurement apparatus 1 transmits ultrasonic waves into a living body (for example, a human body) from the ultrasonic probe 2 by making the ultrasonic probe 2 abut on the surface of the living body. In addition, the ultrasonic waves reflected by an organ within the living body are received by the ultrasonic probe 2, thereby acquiring, for example, an internal tomographic image within the living body or measuring conditions (for example, blood pressure, blood flow, and the like) of an organ within the living body, on the basis of a received signal thereof.

Configuration of Control Device 10

Figure 2:
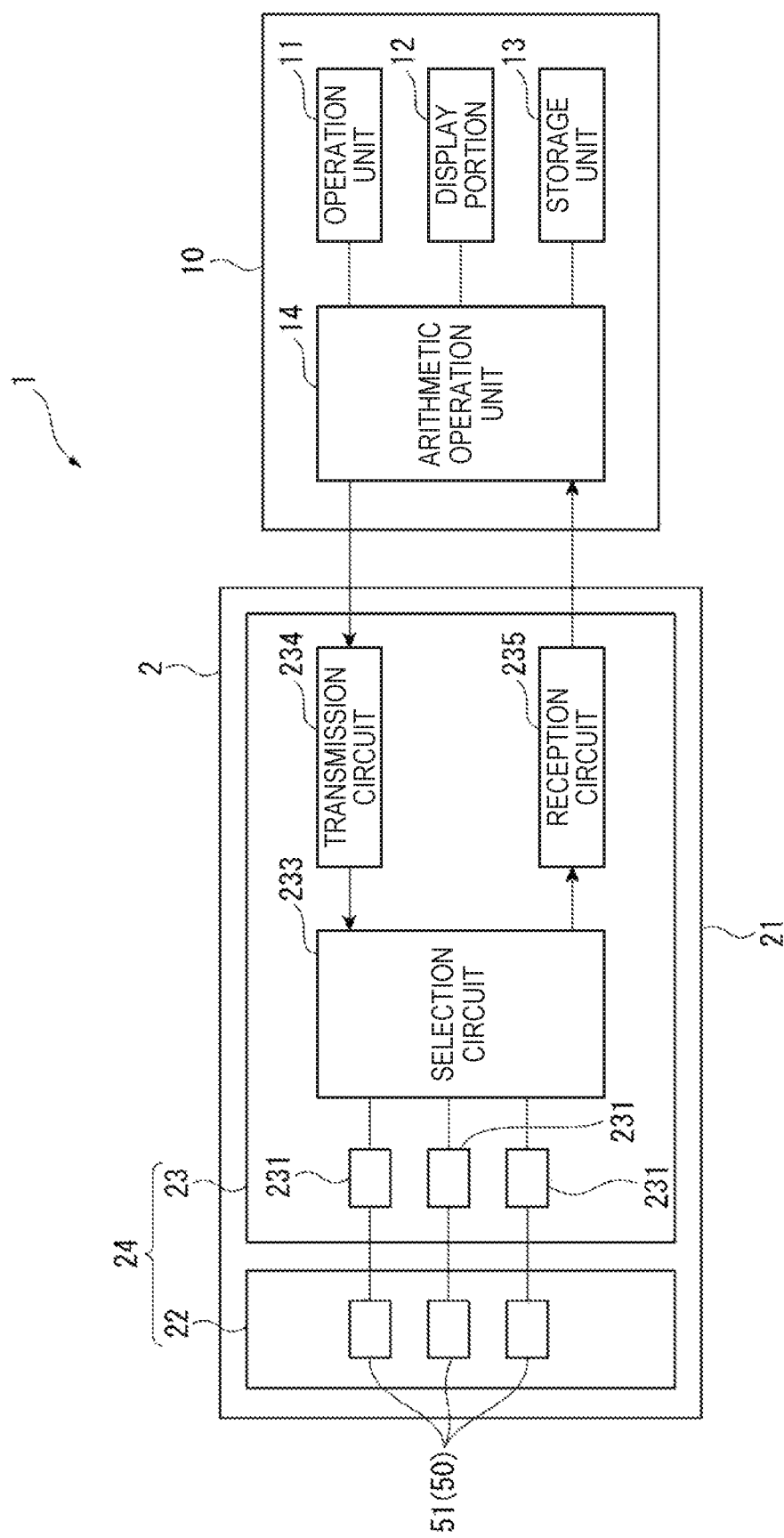
FIG. 2 is a block diagram showing a schematic configuration of the ultrasonic measurement apparatus according to the first embodiment.

FIG. 2 is a block diagram showing a schematic configuration of the ultrasonic measurement apparatus 1.

The control device 10 is configured to include, for example, an operation unit 11, a display portion 12, a storage unit 13, and an arithmetic operation unit 14, as shown in FIG. 2. The control device 10 to be used may be a terminal device such as a tablet terminal, a smart phone, or a personal computer or may be a dedicated terminal device for operating the ultrasonic probe 2.

The operation unit 11 is a user interface (UI) which is used for a user to operate the ultrasonic measurement apparatus 1, and can be constituted by, for example, a touch panel provided on the display portion 12, operation buttons, a keyboard, a mouse, or the like.

The display portion 12 is constituted by, for example, a liquid crystal display or the like, and displays an image.

The storage unit 13 stores various programs and various pieces of data for controlling the ultrasonic measurement apparatus 1.

The arithmetic operation unit 14 is constituted by, for example, an arithmetic circuit such as a central processing unit (CPU), or a storage circuit such as a memory. The arithmetic operation unit 14 reads and executes various programs stored in the storage unit 13 to thereby perform control of generating and outputting a transmission signal to a transmission circuit 234 of the ultrasonic probe 2 and perform control of setting a frequency or a gain of a received signal on a reception circuit 235.

Configuration of Ultrasonic Probe 2

Figure 3:
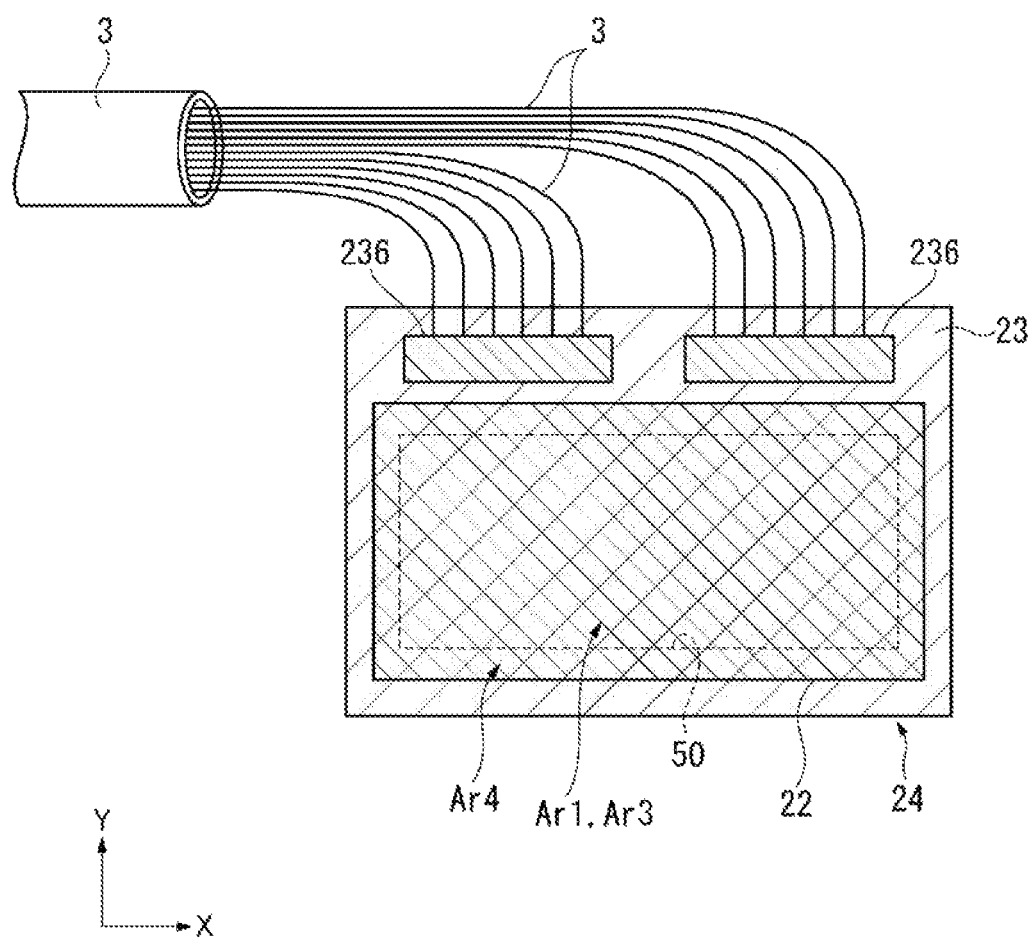
FIG. 3 is a plan view showing a schematic configuration of an ultrasonic sensor in an ultrasonic probe according to the first embodiment.

FIG. 3 is a plan view showing a schematic configuration of the ultrasonic sensor 24 in the ultrasonic probe 2.

The ultrasonic probe 2 includes a housing 21, an ultrasonic device 22 provided inside the housing 21, and a wiring substrate 23 provided with a driver circuit for controlling the ultrasonic device 22, and the like, as shown in FIGS. 1 to 3. Meanwhile, the ultrasonic sensor 24 is constituted by the ultrasonic device 22 and the wiring substrate 23, and the ultrasonic sensor 24 constitutes an ultrasonic module according to the invention.

Configuration of Housing 21

The housing 21 is formed to have a rectangular box shape when seen in a plan view, as shown in FIG. 1, and is configured such that a sensor window 21B is provided on one surface (sensor surface 21A) thereof which is perpendicular to the thickness direction, and a portion of the ultrasonic device 22 is exposed. In addition, a portion (a side surface in the example shown in FIG. 1) of the housing 21 is provided with a passing hole 21C of the cable 3, and the cable 3 is connected to the wiring substrate 23 within the housing 21 from the passing hole 21C. In addition, a gap between the cable 3 and the passing hole 21C is filled with, for example, a resin material, and thus a waterproofing property is secured.

Meanwhile, in this embodiment, a description is given of a configuration example in which the ultrasonic probe 2 and the control device 10 are connected to each other through the cable 3, as shown in FIG. 3, but the invention is not limited thereto. For example, the ultrasonic probe 2 and the control device 10 may be connected to each other through wireless communication, or various components of the control device 10 may be provided within the ultrasonic probe 2.

The ultrasonic device 22 constitutes the ultrasonic sensor 24 together with the wiring substrate 23, as described above. The ultrasonic device 22 includes an ultrasonic transducer array 50 in which a plurality of ultrasonic transducers 51 (see FIG. 4) are arranged in an array, as shown in FIGS. 2 and 3.

Meanwhile, a detailed configuration of the ultrasonic device 22 will be described later.

Configuration of Wiring Substrate 23

The wiring substrate 23 includes a wiring terminal 231, a bonding member 232 (see FIG. 5), a selection circuit 233, a transmission circuit 234, a reception circuit 235, and a connector unit 236, as shown in FIGS. 2 and 3. Among these, the selection circuit 233, the transmission circuit 234, the reception circuit 235, and the connector unit 236 constitute a driver circuit for driving the ultrasonic device 22, or the like, that is, an integrated circuit IC (see FIG. 5). The integrated circuit IC is equivalent to an input and output circuit according to the invention.

A plurality of wiring terminals 231 are disposed on the wiring substrate 23, and are electrically connected to the above-mentioned integrated circuit IC. Each of the plurality of wiring terminals 231 is connected to the ultrasonic transducer 51, more specifically, a first through electrodes 423 or a second through electrodes 424 to be described later through the bonding member 232. Meanwhile, the first through electrode 423 and the second through electrode 424 are equivalent to columnar electrodes (intermediate electrodes) according to the invention.

The selection circuit 233 switches between transmission connection for connecting the ultrasonic device 22 and the transmission circuit 234 to each other and reception connection for connecting the ultrasonic device 22 and the reception circuit 235 to each other under the control of the control device 10.

The transmission circuit 234 outputs a transmission signal indicating that ultrasonic waves are transmitted to the ultrasonic device 22 through the selection circuit 233 at the time of being switched to transmission connection under the control of the control device 10.

The reception circuit 235 outputs a received signal which is input from the ultrasonic device 22 through the selection circuit 233 to the control device 10 at the time of being switched to reception connection under the control of the control device 10. The reception circuit 235, which is configured to include, for example, a low noise amplifier circuit, a voltage control attenuator, a programmable gain amplifier, a low-pass filter, an A/D converter, and the like, performs each signal processing, such as conversion of a received signal into a digital signal, removal of a noise component, and amplification to a desired signal level, and then outputs the processed received signal to the control device 10.

The connector unit 236 is connected to the transmission circuit 234 and the reception circuit 235. In addition, the cable 3 is connected to the connector unit 236, and the cable 3 is drawn from the passing hole 21C of the housing 21 and is connected to the control device 10, as described above.

Configuration of Ultrasonic Device 22

Figure 4:
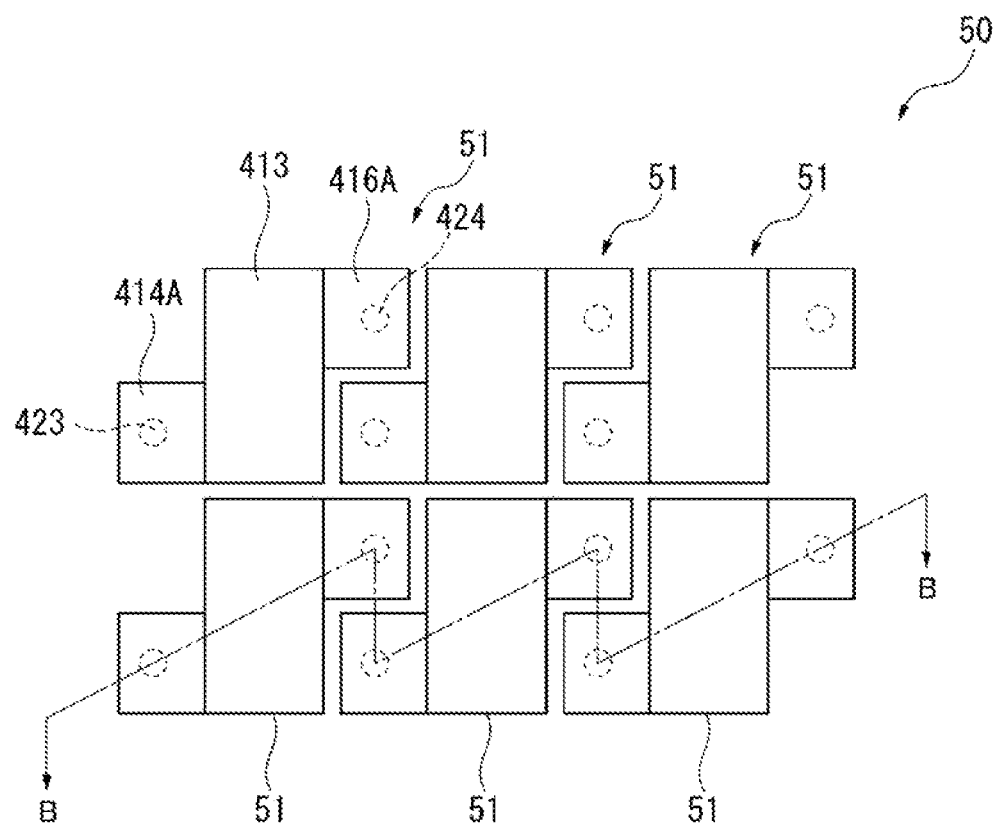
FIG. 4 is an enlarged plan view of a portion of an element substrate of the ultrasonic sensor according to the first embodiment.
Figure 5:
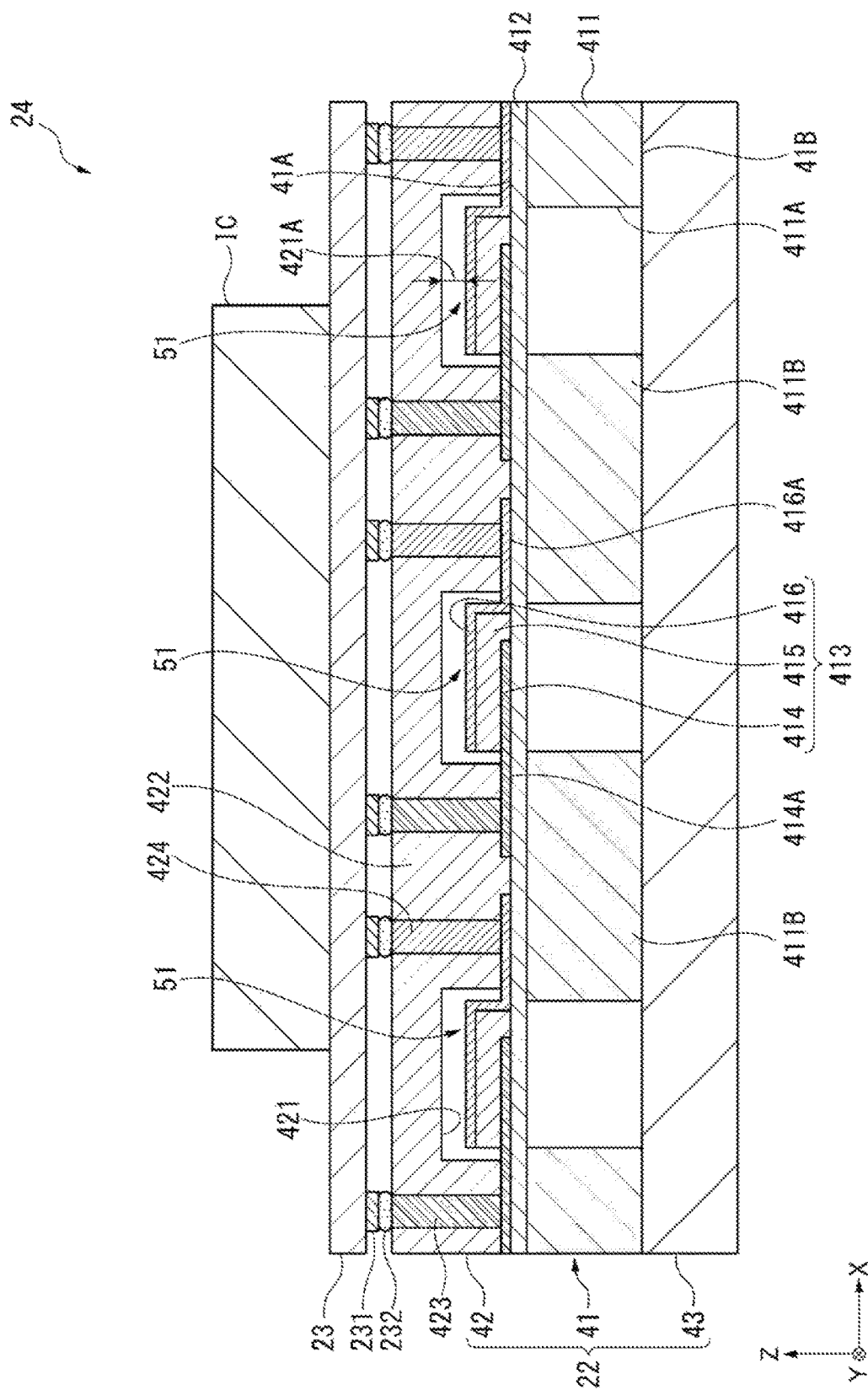
FIG. 5 is a cross-sectional view of a portion of the ultrasonic sensor according to the first embodiment.

FIG. 4 is an enlarged plan view of a portion of an element substrate 41 of the ultrasonic probe 2 according to this embodiment, and FIG. 5 is a cross-sectional view of the element substrate 41 (ultrasonic sensor 24) when a portion of the element substrate 41 in FIG. 4 is taken along line B-B.

The ultrasonic device 22 constituting the ultrasonic sensor 24 is constituted by the element substrate 41, a sealing plate 42, and an acoustic matching layer 43 (see FIG. 5), as shown in FIGS. 3 and 4.

Configuration of Element Substrate 41

The element substrate 41 includes a substrate main body 411, a vibration film 412 laminated on the substrate main body 411, and a piezoelectric element 413 laminated on the vibration film 412, as shown in FIG. 5. Here, the element substrate 41 includes a back surface 41A facing the sealing plate 42, and an operating surface 41B serving as a direction in which ultrasonic waves are transmitted and received on a side opposite to the back surface 41A. In addition, the ultrasonic transducer 51 according to the invention is constituted by the vibration film 412 and the piezoelectric element 413.

As shown in FIG. 4, a central region of the element substrate 41 is provided with the ultrasonic transducer array 50 in which the plurality of ultrasonic transducers 51 are arranged in an array, in a plan view when the element substrate 41 is seen from a thickness direction. Hereinafter, the region provided with the ultrasonic transducer array 50 will be referred to as an array region Ar1 (see FIG. 3).

The substrate main body 411 is a semiconductor substrate such as Si. Openings 411A corresponding to the respective ultrasonic transducers 51 are provided within an array region Ar1 of the substrate main body 411. In addition, the openings 411A are closed by the vibration film 412 provided on the back surface 41A side of the substrate main body 411.

The vibration film 412 is constituted by, for example, $SiO_2$ or a laminated body of $SiO_2$ and $ZrO_2$, and is provided so as to cover the entire back surface 41A side of the substrate main body 411. A thickness dimension of the vibration film 412 is sufficiently smaller than that of the substrate main body 411. In a case where the substrate main body 411 is formed of Si and the vibration film 412 is formed of $SiO_2$, it is possible to easily form the vibration film 412 with a desired thickness dimension, for example, by oxidizing the back surface 41A side of the substrate main body 411. In this case, it is possible to easily form the opening 411A by etching the substrate main body 411 using the vibration film 412 formed of $SiO_2$ as an etching stopper.

Meanwhile, a recessed opening according to the invention is constituted by the opening 411A and a region that closes the opening 411A in the vibration film 412. In addition, a portion which is not provided with the opening 411A in the element substrate 41 is a supporting portion 411B that surrounds the opening 411A when seen in a plan view.

In addition, the piezoelectric element 413 which is a laminated body of a lower electrode 414, a piezoelectric film 415, and an upper electrode 416, which are independently provided, is provided on the vibration film 412 that closes the openings 411A, as shown in FIG. 5. Meanwhile, the piezoelectric element 413 is equivalent to a piezoelectric body according to the invention. In addition, the ultrasonic transducer 51 is constituted by the vibration film 412 and the piezoelectric element 413.

In the ultrasonic transducer 51, a rectangular wave voltage with a predetermined frequency is applied between the lower electrode 414 and the upper electrode 416, and thus it is possible to vibrate the vibration film 412 within an opening region of the opening 411A and to transmit ultrasonic waves. In addition, when the vibration film 412 is vibrated by ultrasonic waves reflected from an object, a potential difference occurs between upper and lower sides of the piezoelectric film 415. Therefore, it is possible to detect received ultrasonic waves by detecting the potential difference occurring between the lower electrode 414 and the upper electrode 416.

In addition, the lower electrode 414 is independently provided for each piezoelectric element 413, and the upper electrode 416 is independently provided for each piezoelectric element 413, similar to the lower electrode 414.

Meanwhile, the first through electrode 423 to be described later is electrically connected to each of the lower electrodes 414, and the second through electrode 424 to be described later is electrically connected to each of the upper electrodes 416.

In addition, in this embodiment, as shown in FIG. 4, the plurality of ultrasonic transducers 51 mentioned above are disposed within the array region Ar1 of the element substrate 41 along an X-direction (first direction) and a Y-direction (second direction) perpendicular to the X-direction.

Specifically, regarding the piezoelectric element 413 constituting the ultrasonic transducer 51 a lower connection electrode 414A (equivalent to a third connection electrode according to the invention) is drawn toward the −X side from an end on the −Y side at an end side on the −X side of the lower electrode 414 that overlaps the piezoelectric film 415, as shown in FIG. 4. In addition, an upper connection electrode 416A (equivalent to a fourth connection electrode according to the invention) is drawn toward the +X side from the +Y side at an end side on the +X side of the upper electrode 416 that overlaps the piezoelectric film 415. That is, in a case where the piezoelectric element 413 is seen along the Y-direction, the upper electrode 416 of the piezoelectric element 413 positioned on the −X side and the lower electrode 414 of the piezoelectric element 413 positioned on the +X side are disposed so as to overlap each other between two piezoelectric elements 413 that are adjacent to each other along the X-direction.

With such a configuration, it is possible to densely dispose the piezoelectric elements 413, as compared to a case where the lower connection electrode 414A is drawn toward the −X side from a central portion of an end side on the −X side of the piezoelectric element 413, and the upper connection electrode 416A is drawn toward the +X side from the central portion of the end side on the +X side (the lower electrode 414 and the upper electrode 416 do not overlap each other when seen along the Y-direction).

Configuration of Sealing Plate 42

The sealing plate 42 is configured such that the planar shape thereof when seen from the thickness direction is the same shape as that of, for example, the element substrate 41, and is constituted by a semiconductor substrate such as a silicon substrate, or an insulating substrate. Meanwhile, the material and thickness of the sealing plate 42 have influence on frequency characteristics of the ultrasonic transducer 51, and thus are preferably set on the basis of the center frequency of ultrasonic waves transmitted and received by the ultrasonic transducer 51.

In the sealing plate 42, a plurality of concave grooves 421 corresponding to the openings 411A of the element substrate 41 are formed in an array counter region Ar3 (See FIG. 3) which faces the array region Ar1 of the element substrate 41. Thereby, in the vibration film 412, a gap 421A having a predetermined dimension is provided with respect to the element substrate 41 in a region (within the opening 411A) which is vibrated by the ultrasonic transducer 51, and thus the vibration of the vibration film 412 is not obstructed. In addition, it is possible to suppress a defect (crosstalk) in which back waves from one ultrasonic transducer 51 are incident on another adjacent ultrasonic transducer 51.

Meanwhile, a region (the supporting portion 411B; see FIG. 5) of the substrate main body 411 other than the opening 411A and a region of the sealing plate 42 other than the concave groove 421 may abut against each other or may be bonded to each other.

In addition, when the vibration film 412 vibrates, ultrasonic waves as back waves are radiated not only to the opening 411A side (operating surface 41B side) but also to the sealing plate 42 side (back surface 41A side). The back waves are reflected by the sealing plate 42, and are radiated to the vibration film 412 side again through the gap 421A. At this time, when phases of the reflected back waves and the ultrasonic waves radiated to the operating surface 41B side from the vibration film 412 deviate, the ultrasonic waves are attenuated. Therefore, in this embodiment, the depth of each of the concave grooves 421 is set so that an acoustic distance in the gap 421A is set to be odd number times a quarter of a wavelength λ (λ/4) of an ultrasonic wave. In other words, the thickness dimension of each portion of the element substrate 41 and the sealing plate 42 is set in consideration of the wavelength λ of the ultrasonic wave emitted from the ultrasonic transducer 51.

In addition, in the sealing plate 42, a reinforcement portion 422 facing the supporting portion 411B is bonded to the element substrate 41 to thereby reinforce the element substrate 41. In the reinforcement portion 422, a through hole is provided at each of positions that face the lower connection electrodes 414A and the upper connection electrodes 416A, and through electrodes (the first through electrode 423 and the second through electrode 424) are provided in the through hole.

The first through electrode 423 passes through the sealing plate 42 in the thickness direction to be connected to the lower connection electrode 414A. The first through electrode 423 is provided corresponding to each of the plurality of lower connection electrodes 414A. Therefore, an independent signal can be input and output with respect to each of the lower electrodes 414 through the lower connection electrode 414A from the first through electrode 423.

Similarly, the second through electrode 424 passes through the sealing plate 42 in the thickness direction to be connected to the upper connection electrode 416A. The second through electrode 424 is provided corresponding to each of the plurality of upper connection electrodes 416A, and an independent signal can be input and output with respect to each of the upper electrodes 416 through the upper connection electrode 416A from the second through electrode 424.

Connection of the first through electrode 423 and the lower connection electrode 414A, and connection of the second through electrode 424 and the upper connection electrode 416A may be performed through bonding using a conductive bonding member (not shown) such as solder, or may be performed through bonding using an anisotropic conductive film (ACF) or anisotropic conductive paste (ACP). In a case where an ACF or ACP is used, the ACF is formed on, for example, a surface facing the element substrate 41 of the reinforcement portion 422 of the sealing plate 42, or the ACP is applied thereto. Then, the sealing plate 42 is superimposed on the element substrate 41 to apply a load in the thickness direction. Thereby, conductivity is held in a load application direction (thickness direction) of the ACF (or ACP), and an insulating property is held in a direction perpendicular to the application of a load. That is, the first through electrode 423 and the lower connection electrode 414A are electrically connected to each other, the second through electrode 424 and the upper connection electrode 416A are electrically connected to each other, and the element substrate 41 and the sealing plate 42 are bonded to each other by an ACF (or ACP).

In addition, the other end sides (sides opposite to the element substrate 41) of the first through electrodes 423 and the second through electrodes 424 are connected to the wiring terminals 231 of the wiring substrate 23 through the conductive bonding member 232 such as solder. The wiring terminals 231 are independently formed on the wiring substrate 23, and are independently controlled by the above-mentioned integrated circuit IC. That is, in this embodiment, the ultrasonic transducers 51 can be independently controlled through the first through electrodes 423 and the second through electrodes 424. In other words, ultrasonic waves can be transmitted at each timing from a CAV surface (surface on a side to which the opening 411A in the element substrate 41 opens) of each of the ultrasonic transducers 51.

In this case, for example, a transmission timing of ultrasonic waves to be transmitted from the ultrasonic transducers 51 lined up in the X-direction is delayed with a direction perpendicular to the X-direction and the Y-direction as a Z-direction (a normal direction of a substrate surface of the element substrate 41 (substrate thickness direction)), and thus it is possible to control a transmission direction of the ultrasonic waves in an XZ plane. In addition, for example, a transmission timing of ultrasonic waves to be transmitted from the ultrasonic transducers 51 lined up in the Y-direction is delayed, and thus it is possible to control a transmission direction of the ultrasonic waves in a YZ plane. That is, the ultrasonic transducer array 50 can be made to function as a two-dimensional array, and thus it is possible to transmit ultrasonic waves in any direction. For this reason, in this embodiment, an acoustic lens that refracts ultrasonic waves to control a transmission direction to a predetermined direction is not provided.

Configuration of Acoustic Matching Layer 43

The acoustic matching layer 43 is provided on the operating surface 41B side of the element substrate 41, as shown in FIG. 5. Specifically, the acoustic matching layer 43 is filled into the opening 411A of the element substrate 41, and is formed to have a predetermined thickness dimension from the operating surface 41B side of the substrate main body 411.

The acoustic matching layer 43 efficiently propagates ultrasonic waves transmitted from the ultrasonic transducer 51 to a living body which is an object to be measured, and efficiently propagates the ultrasonic wave reflected within the living body to the ultrasonic transducer 51. For this reason, the acoustic matching layer 43 is set to intermediate acoustic impedance between acoustic impedance of the ultrasonic transducer 51 of the element substrate 41 and acoustic impedance of the living body.

Operational Effects of First Embodiment

In this embodiment, the element substrate 41 including the lower connection electrode 414A and the upper connection electrode 416A, which are drawn between the piezoelectric element 413 and the adjacent piezoelectric element among the plurality of piezoelectric elements 413 arranged in an array, is provided. In addition, the sealing plate 42 is provided with the first through electrode 423 and the second through electrode 424 which are provided at positions overlapping the lower connection electrode 414A and the upper connection electrode 416A and connect the integrated circuit IC to the lower connection electrode 414A and the upper connection electrode 416A.

In such a configuration, the lower connection electrode 414A and the upper connection electrode 416A are drawn between the piezoelectric elements 413, and the first through electrode 423 and the second through electrode 424 are provided corresponding to the lower connection electrode 414A and the upper connection electrode 416A, respectively. That is, in this embodiment, the first through electrode 423 and the second through electrode 424 which connect the integrated circuit IC to the lower connection electrode 414A and the upper connection electrode 416A of each of the piezoelectric elements 413 are provided within an array region provided with the piezoelectric elements 413 arranged in an array. For this reason, for example, it is not necessary to pull around the connection electrodes to the outside of the array region (outer peripheral end of the element substrate 41), and thus it is possible to achieve the simplification of a wiring configuration. In addition, a terminal region for performing connection of the connection electrodes and a wiring substrate is not required to be provided at the outer peripheral end of the element substrate 41, and thus it is possible to achieve a reduction in the size of the element substrate. Furthermore, since the first through electrode 423 and the second through electrode 424 are configured to be provided within the ultrasonic transducer array 50, the pulling-around of a wiring, and the like are not required, and thus it is possible to reduce the size of the ultrasonic device 22 and to promote reductions in the sizes of the ultrasonic sensor 24 and the ultrasonic probe 2.

In addition, this embodiment adopts a configuration in which a signal is independently input and output with respect to each of the first through electrode 423 and the second through electrode 424 from the integrated circuit IC, and thus it is possible to individually control the piezoelectric elements 413 and to drive the piezoelectric elements 413 with a high level of accuracy.

In other words, in a configuration disclosed in JP-A-2012-152319 described above, a COM (common electrode) and an SIG (driving electrode) are common to a plurality of elements, and the plurality of elements are driven as one element group. In such a configuration, in an element distant from an input position of a signal with respect to the COM and the SIG, a voltage drop of a signal occurs, which results in deterioration in driving accuracy.

On the other hand, in this embodiment, since the piezoelectric elements 413 are independently connected to the integrated circuit IC through the first through electrodes 423 and the second through electrode 424, the above-mentioned voltage drop of a signal does not occur, and thus it is possible to drive the piezoelectric elements 413 with a high level of accuracy. In addition, the piezoelectric elements 413 are independently provided, and are thus allowed to function as a two-dimensional array structure. In other words, the transmission of ultrasonic waves can be controlled for each piezoelectric element 413 (ultrasonic transducer 51), and thus it is possible to control a transmission direction of ultrasonic waves without using, for example, an acoustic lens and the like.

In this embodiment, the lower connection electrode 414A is drawn from the −Y side to the −X side at an end side on the −X side of the piezoelectric element 413. In addition, the upper connection electrode 416A is drawn from the +Y side to the +X side at an end side on the +X side of the piezoelectric element 413. Accordingly, in piezoelectric elements 413 (ultrasonic transducers 51) that are adjacent to each other in the X-direction, an upper connection electrode 416A of the piezoelectric element 413 disposed on the −X side and a lower connection electrode 414A of the piezoelectric element 413 disposed on the +X side can be disposed side by side along the Y-direction. With such a configuration, in the ultrasonic transducer array 50, it is possible to densely dispose the ultrasonic transducers 51, to make the ultrasonic transducer array 50 and the ultrasonic device 22 smaller, and to promote further reductions in the sizes of the ultrasonic sensor 24 and the ultrasonic probe 2.

The ultrasonic probe 2 in this embodiment is a so-called CAV surface emitting ultrasonic probe that transmits ultrasonic waves from a CAV surface, and the piezoelectric element 413, the lower connection electrode 414A, and the upper connection electrode 416A are disposed on a side opposite to an ultrasonic wave emission side in the vibration film 412. In a case where the measurement of ultrasonic waves is performed on a living body using the ultrasonic probe 2, gel is applied between the acoustic matching layer 43 and the living body, but drops of water may be normally infiltrated between the acoustic matching layer 43 and the vibration film 412. However, as described above, in this embodiment, the piezoelectric element 413, the lower connection electrode 414A, and the upper connection electrode 416A are disposed on the back surface 41A side of the vibration film 412, and thus do not come into contact with drops of water, and thus it is possible to suppress defects such as a short-circuit and rust.

Second Embodiment

Next, a second embodiment of the invention will be described.

An ultrasonic measurement apparatus according to this embodiment has substantially the same configuration as that of the ultrasonic measurement apparatus 1 described above, and is different from the ultrasonic measurement apparatus 1 in that a portion of a configuration of a piezoelectric element 413 constituting an ultrasonic transducer is different.

Meanwhile, in the following description, components that are the same as or substantially the same as those of the ultrasonic measurement apparatus 1 according to the first embodiment will be denoted by the same reference numerals and signs, and a description thereof will be omitted or simplified.

Figure 6:
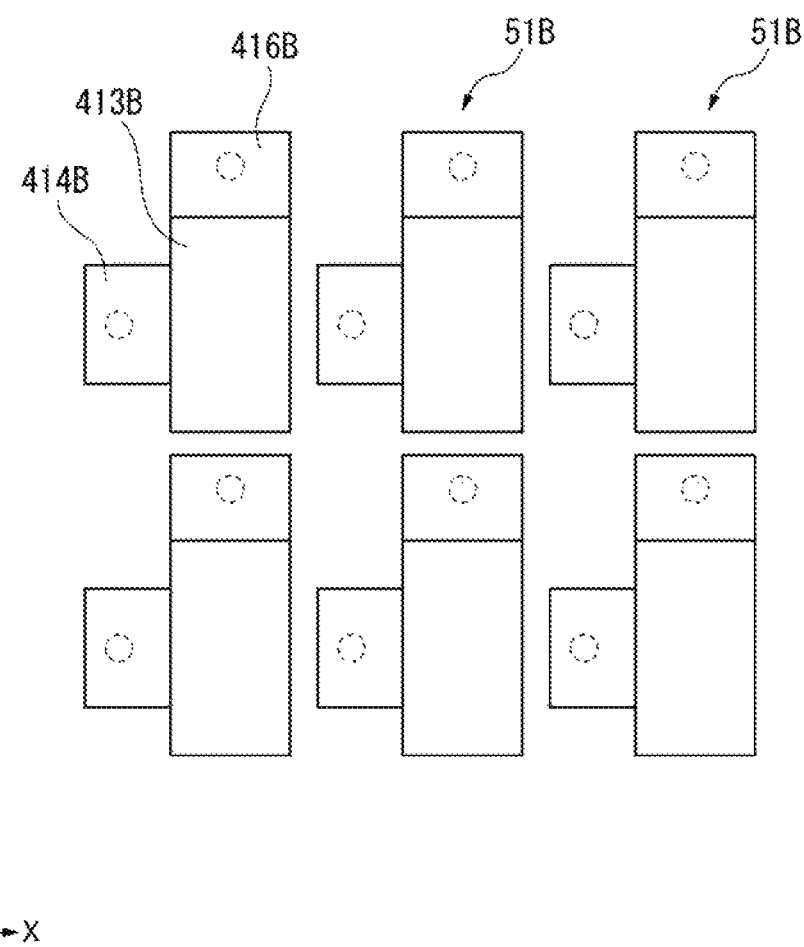
FIG. 6 is an enlarged plan view of a portion of an element substrate of an ultrasonic sensor of an ultrasonic measurement apparatus according to a second embodiment.

FIG. 6 is an enlarged plan view of a portion of an element substrate of an ultrasonic sensor of the ultrasonic measurement apparatus according to this embodiment.

In this embodiment, as shown in FIG. 6, a plurality of ultrasonic transducers 51B mentioned above are disposed along an X-direction (first direction) and a Y-direction (second direction) which is perpendicular to the X-direction within an array region Ar1 of an element substrate 41.

In this embodiment, a lower connection electrode 414B is drawn to the −X side of a lower electrode 414 that overlaps a piezoelectric film 415 in FIG. 6. On the other hand, an upper connection electrode 416B is drawn to the +Y side of an upper electrode 416 that overlaps the piezoelectric film 415. In this embodiment, the lower connection electrode 414B is equivalent to a first connection electrode according to the invention, and the upper connection electrode 416B is equivalent to a second connection electrode according to the invention.

Meanwhile, in the above-mentioned example, a description is given of an example in which the lower connection electrode 414B is drawn to the −X side of the lower electrode 414, and the upper connection electrode 416B is drawn to the +Y side of the upper electrode 416, but the invention is not limited thereto.

For example, the lower connection electrode 414B may be drawn to the −X side of the lower electrode 414, the upper connection electrode 416B may be drawn to the −Y side of the upper electrode 416, the lower connection electrode 414B may be drawn to the +X side of the lower electrode 414, the upper connection electrode 416B may be drawn to the −Y side of the upper electrode 416, the lower connection electrode 414B may be drawn to the +X side of the lower electrode 414, and the upper connection electrode 416B may be drawn to the +Y side of the upper electrode 416.

In addition, drawing directions of the lower connection electrode 414B and the upper connection electrode 416B may be switched to each other. For example, the lower connection electrode 414B may be drawn to the −Y side of the lower electrode 414, the upper connection electrode 416B may be drawn to the +X side of the upper electrode 416, the lower connection electrode 414B may be drawn to the −Y side of the lower electrode 414, the upper connection electrode 416B may be drawn to the −X side of the upper electrode 416, the lower connection electrode 414B may be drawn to the +Y side of the lower electrode 414, the upper connection electrode 416B may be drawn to the −X side of the upper electrode 416, the lower connection electrode 414B may be drawn to the +Y side of the lower electrode 414, and the upper connection electrode 416B may be drawn to the +X side of the upper electrode 416.

Operational Effects of Second Embodiment

In this embodiment, a piezoelectric element 413B constituting the ultrasonic transducer 51B includes the lower connection electrode 414B which is drawn to the −X side and the upper connection electrode 416B which is drawn to the +Y side. In this case, when piezoelectric elements 413C are arranged along the X-direction and the Y-direction, one lower connection electrode 414B is disposed between piezoelectric elements 413B that are aligned in the X-direction, and one upper connection electrode 416B is disposed between piezoelectric elements 413B that are aligned in the Y-direction. Accordingly, it is possible to densely dispose the piezoelectric elements 413B (ultrasonic transducers 51B), for example, as compared to a case where a plurality of (for example, two) connection electrodes are disposed between piezoelectric elements. Thereby, similarly to the above-described first embodiment, it is possible to make an ultrasonic transducer array 50 and an ultrasonic device 22 smaller and to promote further reductions in the sizes of an ultrasonic sensor 24 and an ultrasonic probe 2.

Third Embodiment

Next, a third embodiment of the invention will be described.

An ultrasonic measurement apparatus according to this embodiment has substantially the same configuration as that of the ultrasonic measurement apparatus 1 described above, and is different from the ultrasonic measurement apparatus 1 in that a portion of a configuration of a piezoelectric element 413 constituting an ultrasonic transducer is different.

Meanwhile, in the following description, components that are the same as or substantially the same as those of the ultrasonic measurement apparatus 1 according to the first embodiment will be denoted by the same reference numerals and signs, and a description thereof will be omitted or simplified.

Figure 7:
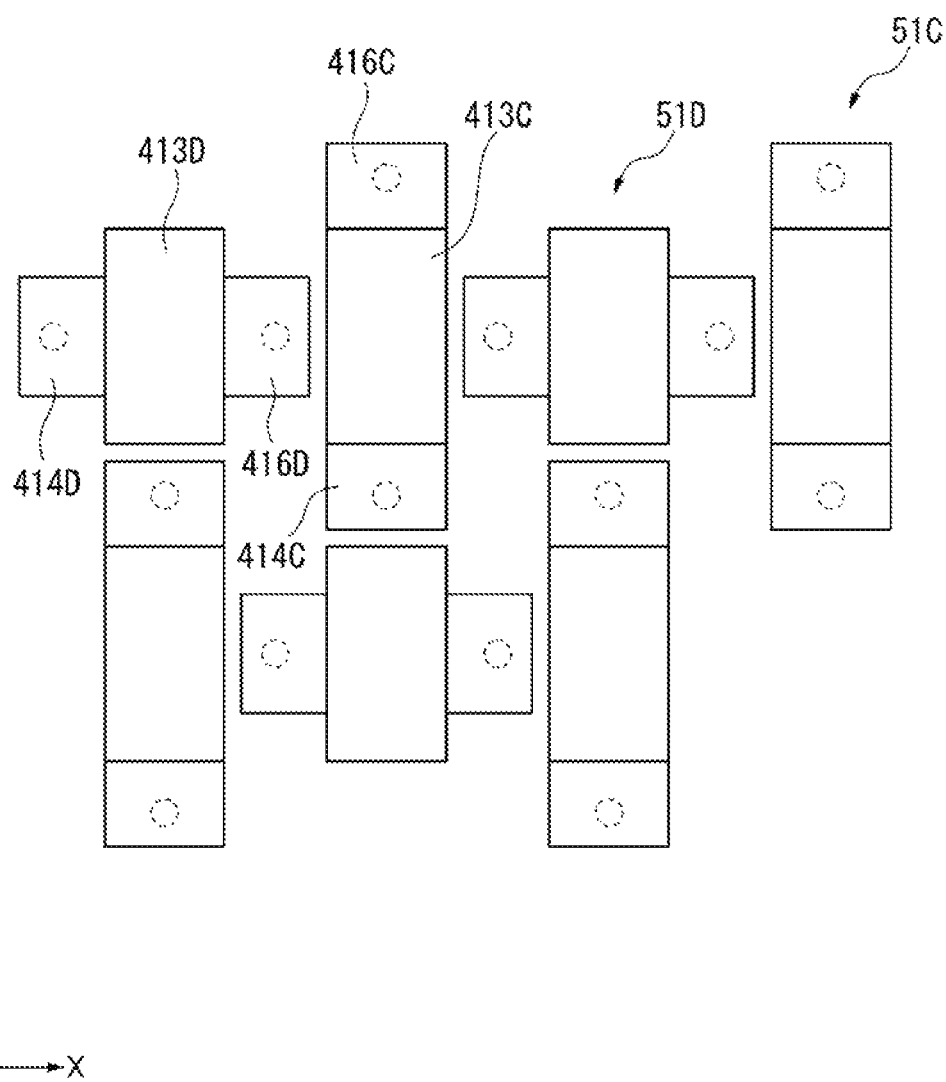
FIG. 7 is an enlarged plan view of a portion of an element substrate of an ultrasonic sensor of an ultrasonic measurement apparatus according to a third embodiment.

FIG. 7 is an enlarged plan view of a portion of an element substrate of an ultrasonic sensor of the ultrasonic measurement apparatus according to the embodiment.

In this embodiment, as shown in FIG. 7, a plurality of ultrasonic transducers 51C and 51D are disposed along an X-direction (first direction) and a Y-direction (second direction) which is perpendicular to the X-direction within an array region Ar1 of an element substrate 41.

Specifically, as shown in FIG. 7, in a piezoelectric element 413C constituting the ultrasonic transducer 51C, a lower connection electrode 414C is drawn to a −Y side of a lower electrode 414 that overlaps a piezoelectric film 415, and an upper connection electrode 416C is drawn to the +Y side of an upper electrode 416 that overlaps the piezoelectric film 415.

On the other hand, in a piezoelectric element 413D constituting the ultrasonic transducer 51D, a lower connection electrode 414D is drawn to the −X side of the lower electrode 414 that overlaps the piezoelectric film 415, and an upper connection electrode 416D is drawn to the +X side from the upper electrode 416 that overlaps the piezoelectric film 415. In this embodiment, the piezoelectric element 413D is equivalent to a first piezoelectric element according to the invention, and the piezoelectric element 413C is equivalent to a second piezoelectric element according to the invention.

Meanwhile, in the above-mentioned example, the lower connection electrode 414C is drawn to the −Y side and the upper connection electrode 416C is drawn to the +Y side in the piezoelectric element 413C, but the lower connection electrode 414C may be drawn to the +Y side, and the upper connection electrode 416C may be drawn to the −Y side. Similarly, the lower connection electrode 414D is drawn to the −X side and the upper connection electrode 416D is drawn to the +X side in the piezoelectric element 413D, the lower connection electrode 414D may be drawn to the +X side, and the upper connection electrode 416D may be drawn to the −X side.

Operational Effects of Third Embodiment

In this embodiment, the lower connection electrode 414C and the upper connection electrode 416C are drawn along the Y-direction in the piezoelectric element 413C constituting the ultrasonic transducer 51C out of the ultrasonic transducers 51C and 51D, and the lower connection electrode 414D and the upper connection electrode 416D are drawn along the X-direction in the piezoelectric element 413D constituting the ultrasonic transducer 51D. The ultrasonic transducers 51C and 51D are alternately disposed in the X-direction and the Y-direction. In such a configuration, one lower connection electrode 414C or one upper connection electrode 416C is disposed between piezoelectric elements 413C that are aligned in the X-direction, and one lower connection electrode 414D or one upper connection electrode 416D is disposed between piezoelectric elements 413D that are aligned in the Y-direction. Accordingly, it is possible to densely dispose the piezoelectric elements 413C and 413D (ultrasonic transducers 51C and 51D), for example, as compared to a case where a plurality of (for example, two) connection electrodes are disposed between piezoelectric elements. Thereby, similarly to the above-described first embodiment, it is possible to make an ultrasonic transducer array 50 and an ultrasonic device 22 smaller and to promote further reductions in the sizes of an ultrasonic sensor 24 and an ultrasonic probe 2.

Fourth Embodiment

Next, a fourth embodiment of the invention will be described.

An ultrasonic measurement apparatus according to this embodiment has substantially the same configuration as that of the ultrasonic measurement apparatus 1 described above, and is different from the ultrasonic measurement apparatus 1 in terms of a configuration of an ultrasonic sensor. Specifically, in the first embodiment, a sealing plate 42 is provided so as to face a vibration film 412 of an element substrate 41, but the fourth embodiment is different from the above-described first embodiment in that a sealing plate 42E is provided so as to face an opening 411E1 of an element substrate 41E. That is, in the first embodiment, each of the ultrasonic transducers 51 transmits (CAV surface emission) ultrasonic waves from an opening 411A of the element substrate 41, and receives ultrasonic waves that are input to the vibration film 412 from the opening 411A. On the other hand, in this embodiment, each ultrasonic transducer transmits (ACT surface emission) ultrasonic waves to a side opposite to the opening 411E1, and receives ultrasonic waves that are input from the side opposite to the opening 411E1. In addition, in this embodiment, the arrangement (array structure) of the ultrasonic transducers is similar to that of the ultrasonic transducers 51 shown in FIG. 4.

Meanwhile, in the following description, components that are the same as or substantially the same as those of the ultrasonic measurement apparatus 1 according to the first embodiment will be denoted by the same reference numerals and signs, and a description thereof will be omitted or simplified.

Figure 8:
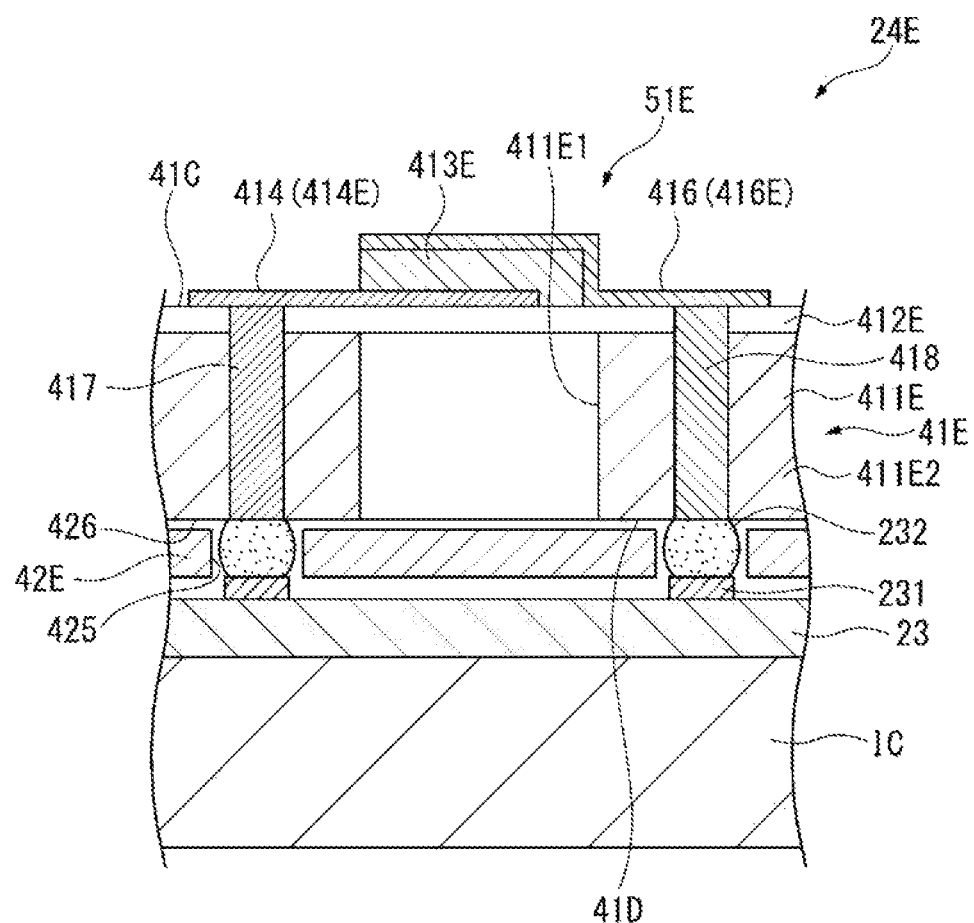
FIG. 8 is a cross-sectional view of a portion of an ultrasonic sensor of an ultrasonic measurement apparatus according to a fourth embodiment.

FIG. 8 is a cross-sectional view of the element substrate 41E (ultrasonic sensor 24E) in this embodiment. Meanwhile, in FIG. 8, an acoustic matching layer 43 mentioned above is disposed so as to cover a piezoelectric element 413E side of the vibration film 412, but is not shown in the drawing.

The ultrasonic sensor 24E includes the element substrate 41E, the sealing plate 42, a wiring substrate 23, an integrated circuit IC, and an acoustic matching layer (not shown).

Configuration of Element Substrate 41E

The element substrate 41E includes a substrate main body 411E, a vibration film 412E laminated on the substrate main body 411E, and the piezoelectric element 413E laminated on the vibration film 412E, as shown in FIG. 8.

Here, in the element substrate 41E, a surface having the piezoelectric element 413E disposed thereon is an operating surface 41C, and the wiring substrate 23 is disposed on a back surface 41D side opposite to the operating surface 41C. In addition, an ultrasonic transducer 51E according to the invention is constituted by the vibration film 412E and the piezoelectric element 413E.

The substrate main body 411E is a semiconductor substrate of Si, for example, and the openings 411E1 corresponding to the respective ultrasonic transducers 51E are provided within an array region Ar1 of the substrate main body 411E. In addition, each of the openings 411E1 is closed by the vibration film 412E provided on the back surface 41D side of the substrate main body 411E.

The vibration film 412E is formed of, for example, $SiO_2$, a laminated body of $SiO_2$ and $ZrO_2$, or the like, and is provided so as to cover the entire back surface 41D side of the substrate main body 411E.

Meanwhile, in the element substrate 41E, a portion which is not provided with the opening 411E1 is a supporting portion 411E2 that surrounds the opening 411E1 when seen in a plan view.

In addition, a piezoelectric element 413E which is a laminated body of a lower electrode 414, a piezoelectric film 415, and an upper electrode 416, which are independent of each other, is provided on the vibration film 412E that closes the openings 411E1, as shown in FIG. 8. Meanwhile, the piezoelectric element 413E is equivalent to a piezoelectric body according to the invention. In addition, the ultrasonic transducer 51E is constituted by the vibration film 412E and the piezoelectric element 413E.

The piezoelectric element 413E constituting the ultrasonic transducer 51E is configured such that a lower connection electrode 414E (equivalent to a third connection electrode according to the invention) is drawn toward the −X side from an end on the −Y side at an end side on the −X side of the lower electrode 414 that overlaps the piezoelectric film 415, similar to the piezoelectric element 413 of the above-described first embodiment. In addition, an upper connection electrode 416E (equivalent to a fourth connection electrode according to the invention) is drawn toward the +X side from the +Y side at an end side on the +X side of the upper electrode 416 that overlaps the piezoelectric film 415.

In addition, in the supporting portion 411E2 of the substrate main body 411E, a through hole is provided at each of positions that face the lower connection electrodes 414E and the upper connection electrodes 416E, and a first columnar electrode 417 and a second columnar electrode 418 as columnar electrodes (intermediate electrodes) are provided in the through hole.

The first columnar electrode 417 passes through the substrate main body 411E in the thickness direction to be connected to the lower connection electrode 414E. The first columnar electrode 417 is provided corresponding to each of the plurality of lower connection electrodes 414E. Therefore, an independent signal can be input and output to each of the lower electrodes 414 through the lower connection electrode 414E from the first columnar electrode 417.

Similarly, the second columnar electrode 418 passes through the substrate main body 411E in the thickness direction to be connected to the upper connection electrode 416E. The second columnar electrode 418 is provided corresponding to each of the plurality of upper connection electrodes 416E, and an independent signal can be input and output to each of the upper electrodes 416 through the upper connection electrode 416E from the second columnar electrode 418.

Configuration of Sealing Plate 42E

Figure 9:
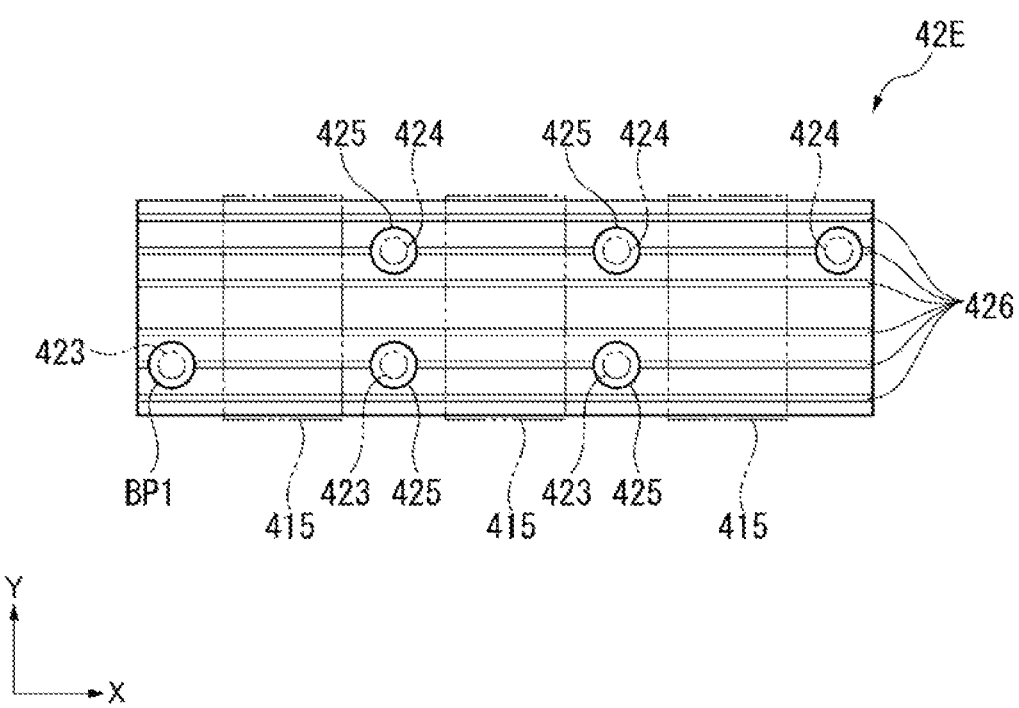
FIG. 9 is a plan view of a back plate of the ultrasonic measurement apparatus according to the fourth embodiment.

FIG. 9 is a plan view when the sealing plate 42E is seen from the element substrate 41E side.

The sealing plate 42 is disposed at a position facing the back surface 41D of the element substrate 41E, and has a function of reinforcing the element substrate 41E. The sealing plate 42 includes a plurality of openings 425 and a plurality of grooves 426, as shown in FIGS. 8 and 9.

Among these, the plurality of openings 425 are disposed at positions corresponding to the first columnar electrode 417 and the second columnar electrode 418. The bonding member 232 for bonding the wiring terminal 231 and each of the first columnar electrode 417 and the second columnar electrode 418 to each other is disposed within each of the plurality of openings 425. Thereby, a signal (power) from the wiring terminal 231 of the wiring substrate 23 is transmitted to the first columnar electrode 417 and the second columnar electrode 418 through the bonding member 232.

Each of the plurality of grooves 426 has a shape that extends along the X-direction of a back plate BP. The plurality of grooves 426 have a function of discharging gas within each of the plurality of openings 425 when the wiring terminal 231 is bonded to each of the first columnar electrode 417 and the second columnar electrode 418 through the bonding member 232.

Operational Effects of Fourth Embodiment

Also in this embodiment, the same operational effects as those of the ultrasonic measurement apparatus 1 of the above-described first embodiment are exhibited. That is, in this embodiment, the element substrate 41E including the lower connection electrode 414E and the upper connection electrode 416E, which are drawn between the piezoelectric element 413E and the adjacent piezoelectric element among the plurality of piezoelectric elements 413E arranged in an array, is provided. In addition, the element substrate 41E is provided with the first columnar electrode 417 and the second columnar electrode 418 which are provided at positions overlapping the lower connection electrode 414A and the upper connection electrode 416A and connect the integrated circuit IC to the lower connection electrode 414A and the upper connection electrode 416A.

In such a configuration, the lower connection electrode 414A and the upper connection electrode 416E are drawn between the piezoelectric elements 413E, and the first columnar electrode 417 and the second columnar electrode 418 are provided corresponding to the lower connection electrode 414E and the upper connection electrode 416E, respectively. That is, in this embodiment, the first columnar electrode 417 and the second columnar electrode 418 which connect the integrated circuit IC to the lower connection electrode 414E and the upper connection electrode 416E of each of the piezoelectric elements 413E are provided within an array region provided with the piezoelectric elements 413E arranged in an array. For this reason, similarly to the first to third embodiments, it is not necessary to pull around the connection electrodes to the outside of the array region (outer peripheral end of the element substrate 41), and thus it is possible to achieve the simplification of a wiring configuration. In addition, a terminal region for performing connection of the connection electrodes and a wiring substrate is not required to be provided at the outer peripheral end of the element substrate 41E, and thus it is possible to achieve a reduction in the size of the element substrate 41E. Furthermore, since the first columnar electrode 417 and the second columnar electrode 418 are configured to be provided within an ultrasonic transducer array 50, the pulling-around of a wiring, and the like are not required, and thus it is possible to reduce the size of an ultrasonic device 22 and to promote reductions in the sizes of an ultrasonic sensor 24 and an ultrasonic probe 2.

In addition, the plurality of grooves 426 are provided, and thus it is possible to reliably discharge gas within the opening 425 when the wiring terminal 231 is bonded to each of the first columnar electrode 417 and the second columnar electrode 418 through the bonding member 232.

Modification Example

Meanwhile, the invention is not limited to the above-described embodiments, and configurations obtained by modification, correction, and an appropriate combination of the embodiments within a range in which the object of the invention can be accomplished are included in the invention.

In the above-described fourth embodiment, the sealing plate 42E is provided, but the invention is not limited thereto. For example, the sealing plate 42 may not be provided. In this case, for example, a configuration in which the element substrate 41 is reinforced by the wiring substrate 23 may be adopted. In such a configuration, since the sealing plate 42E is not provided, it is possible to reduce the thickness dimension of the ultrasonic sensor and to further reduce the size of the ultrasonic measurement apparatus.

In the above-described fourth embodiment, the ultrasonic transducers are disposed in the same manner as the ultrasonic transducers 51 shown in FIG. 4. However, the invention is not limited thereto. For example, in the fourth embodiment, the arrangement of the ultrasonic transducers may be performed in the same manner as in the arrangement (the same arrangement as in the second embodiment) which is shown in FIG. 6, or may be performed in the same manner as in the arrangement (the same arrangement as in the third embodiment) which is shown in FIG. 7.

In the above-described embodiments, a description has been given of an example in which the piezoelectric element 413 is constituted by a laminated body in which the lower electrode 414, the piezoelectric film 415, and the upper electrode 416 are laminated in the thickness direction, but the invention is not limited thereto. For example, a configuration may also adopted in which a pair of electrodes are disposed on one surface side perpendicular to the thickness direction of the piezoelectric element 413 so as to face each other. In addition, electrodes may be disposed so that the piezoelectric film 415 is interposed between side surfaces along the thickness direction of the piezoelectric film 415.

In the above-described embodiments, a configuration in which the integrated circuit IC is provided on the wiring substrate 23 has been described, but the invention is not limited thereto. For example, a configuration may also be adopted in which the integrated circuit IC is provided within the control device 10, and the wiring substrate 23 is provided with a connector unit in which wirings from the respective wiring terminals 231 are integrated. In this case, a cable line may be connected to the connector unit, and the integrated circuit IC of the control device 10 and the ultrasonic probe 2 may be connected to each other through the cable line.

The ultrasonic measurement apparatus 1 is configured to measure an internal tomographic structure of a living body, but can also be used as a measurement apparatus for inspecting a concrete internal structure such as a concrete building.

In addition, the ultrasonic measurement apparatus 1 including the ultrasonic device 22 has been described, but the invention can also be applied to other electronic apparatuses. For example, the invention can be used for an ultrasonic cleaning machine that transmits ultrasonic waves to an object to be cleaned to clean the object to be cleaned using ultrasonic waves.

Figure 10:
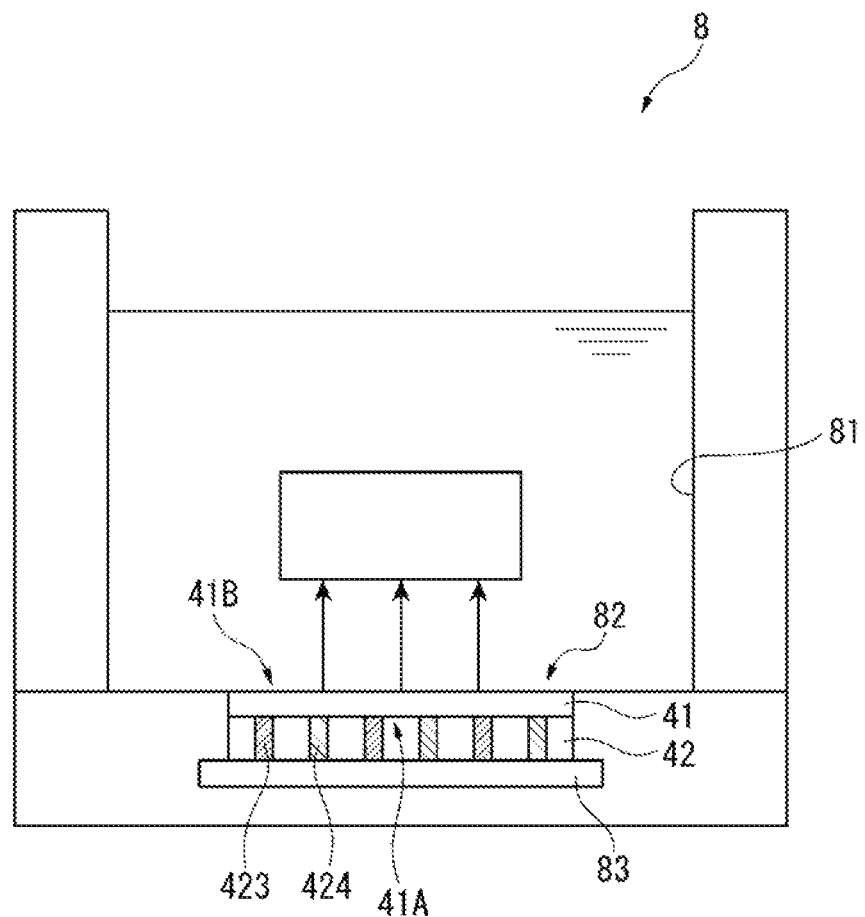
FIG. 10 is a diagram showing an example of an electronic apparatus according to another embodiment.

FIG. 10 is a diagram showing a schematic configuration of an ultrasonic cleaning machine.

An ultrasonic cleaning machine 8 shown in FIG. 10 includes a cleaning tank 81, and an ultrasonic module 82 which is installed on, for example, the bottom face of the cleaning tank 81.

The ultrasonic module 82 includes an ultrasonic device 22 which is the same as that in the above-described first embodiment, and a wiring substrate 83 that controls the ultrasonic device 22. That is, the ultrasonic device 22 includes an element substrate 41 in which an operating surface 41B faces the inner surface of the cleaning tank 81, a sealing plate 42 which is provided on a back surface 41A side of the element substrate 41, and an ultrasonic transducer array 50 (not shown in FIG. 10) which is constituted by a plurality of ultrasonic transducers 51 (not shown in FIG. 10) and is provided on the back surface 41A side of the element substrate 41. An upper electrode 416 of a piezoelectric element 413 constituting the ultrasonic transducer 51 is connected to a first through electrode 423 provided in the sealing plate 42, and a lower electrode 414 is connected to a second through electrode 424. The first through electrode 423 and the second through electrode 424 are electrically connected to a wiring terminal (not shown) which is provided in a wiring substrate 83.

In such a configuration, the ultrasonic device 22 can be easily mounted on the wiring substrate 83 by face-down mounting. In addition, since the operating surface 41B side of the element substrate 41 faces the cleaning tank 81 side, it is possible to increase waterproofing properties of the ultrasonic transducer 51 provided on the back surface 41A side and electrode wires.

In the above-described embodiments, a configuration in which the element substrate 41 is provided with the opening 411A has been described. However, for example, a configuration may also be adopted in which the element substrate 41 is not provided with the opening 411A, ultrasonic waves are transmitted by the ultrasonic transducer 51 vibrating the element substrate 41 itself, and the reception of ultrasonic waves is detected by the vibration of the element substrate 41.

In the above-described embodiments, a description has been given of a configuration in which the vibration film 412 is provided on the back surface 41A side of the substrate main body 411 provided with the opening 411A, but the invention is not limited thereto. For example, a configuration may also be adopted in which a plurality of concave grooves corresponding to the respective ultrasonic transducers 51 are provided on the operating surface 41B side of the substrate main body 411, and the bottom face of the concave groove is configured as a vibration film.

In addition, a configuration in which the vibration film 412 is provided on the back surface 41A side of the opening 411A has been described. However, for example, a configuration may also be adopted in which the vibration film 412 is provided on the operating surface 41B side of the opening 411A, and the piezoelectric element 413 constituting the ultrasonic transducer 51 is provided on the back surface 41A side of the vibration film 412.

In addition, in the ultrasonic transducers 51, 51B, and 51C in the above-described first to third embodiments, the piezoelectric film 415 is formed on the vibration film 412 that covers the opening 411A of the element substrate 41, ultrasonic waves are transmitted by driving the piezoelectric film 415 or ultrasonic waves are received by detecting the displacement of the vibration film 412. On the other hand, the vibration film 412 may be vibrated using another driving method, or the vibration of the vibration film 412 may be detected without using the piezoelectric film 415. For example, a configuration may also be adopted in which a first electrode is disposed on a substrate, a vibration film is disposed with a predetermined air gap with respect to the first electrode, and a second electrode is provided in the vibration film so as to face the first electrode. In this case, a pulse drive voltage is applied between the first electrode and the second electrode, and thus it is possible to output ultrasonic waves by driving the vibration film using an electrostatic force. In addition, when the vibration film vibrates by ultrasonic waves, capacitance between the first electrode and the second electrode changes, and thus it is possible to detect the reception of ultrasonic waves from the change in capacitance.

In addition, a specific structure at the time of implementing the invention may be configured by appropriately combining the above-described embodiments and the modification example within a range in which the object of the invention can be accomplished, or may be appropriately changed to another structure, or the like.

The entire disclosure of Japanese Patent Application No. 2015-234290 filed Nov. 30, 2015 is expressly incorporated by reference herein.

What is claimed is:

1. A piezoelectric module comprising:
   an element substrate that includes a plurality of piezoelectric bodies arranged in an array, and a plurality of connection electrodes that are connected to the piezoelectric body and are drawn between the piezoelectric body and an adjacent piezoelectric body;
   an input and output circuit that is provided on one surface side of the element substrate and independently inputs and outputs a signal from and to each of the connection electrodes; and
   columnar electrodes each of which is provided between each of the connection electrodes and the input and output circuit and connects each of the connection electrodes and the input and output circuit to each other.

2. The piezoelectric module according to claim 1,
   wherein the piezoelectric bodies are arranged in an array along a first direction and a second direction intersecting the first direction when seen in a plan view, and
   wherein the connection electrode includes a first connection electrode which is drawn from the piezoelectric body along the first direction, and a second connection electrode which is drawn from the piezoelectric body along the second direction.

3. The piezoelectric module according to claim 1,
   wherein the piezoelectric bodies are arranged in an array along a first direction and a second direction intersecting the first direction when seen in a plan view,
   wherein the connection electrode includes a third connection electrode which is drawn to one end side of the piezoelectric body in the first direction, and a fourth connection electrode which is drawn to the other end side of the piezoelectric body in the first direction, and wherein the third connection electrode is positioned on one end side in the second direction, and the fourth connection electrode is positioned on the other end side in the second direction.

4. The piezoelectric module according to claim 1,
wherein the piezoelectric bodies are arranged in an array along a first direction and a second direction intersecting the first direction when seen in a plan view,
wherein the connection electrode which is connected to a first piezoelectric body, among the plurality of piezoelectric bodies, is drawn from the piezoelectric body along the first direction, and
wherein the connection electrode which is connected to a second piezoelectric body adjacent to the first piezoelectric body is drawn from the piezoelectric body along the second direction.

5. An ultrasonic module comprising:
an ultrasonic transducer substrate that includes a plurality of ultrasonic transducers arranged in an array, and a plurality of connection electrodes that are connected to the ultrasonic transducer and are drawn between the ultrasonic transducer and an adjacent ultrasonic transducer;
an input and output circuit that is provided on one surface side of the ultrasonic transducer substrate and independently inputs and outputs a signal from and to each of the connection electrodes; and
columnar electrodes each of which is provided between each of the connection electrodes and the input and output circuit and connects each of the connection electrodes and the input and output circuit to each other.

6. The ultrasonic module according to claim 5,
wherein the ultrasonic transducers are arranged in an array along a first direction and a second direction intersecting the first direction when seen in a plan view, and
wherein the connection electrode includes a first connection electrode which is drawn from the ultrasonic transducer along the first direction, and a second connection electrode which is drawn from the ultrasonic transducer along the second direction.

7. The ultrasonic module according to claim 5,
wherein the ultrasonic transducers are arranged in an array along a first direction and a second direction intersecting the first direction when seen in a plan view,
wherein the connection electrode includes a third connection electrode which is drawn to one end side of the ultrasonic transducer in the first direction, and a fourth connection electrode which is drawn to the other end side of the ultrasonic transducer in the first direction, and
wherein the third connection electrode is positioned on one end side in the second direction, and the fourth connection electrode is positioned on the other end side in the second direction.

8. The ultrasonic module according to claim 5,
wherein the ultrasonic transducers are arranged in an array along a first direction and a second direction intersecting the first direction when seen in a plan view,
wherein the connection electrode which is connected to a first ultrasonic transducer, among the plurality of ultrasonic transducers, is drawn from the ultrasonic transducer along the first direction, and
wherein the connection electrode which is connected to a second ultrasonic transducer adjacent to the first ultrasonic transducer is drawn from the ultrasonic transducer along the second direction.

9. An electronic apparatus comprising:
a piezoelectric body substrate that includes a plurality of piezoelectric bodies arranged in an array, and a plurality of connection electrodes that are connected to the piezoelectric body and are drawn between the piezoelectric body and an adjacent piezoelectric body;
columnar electrodes that are provided at positions overlapping the respective connection electrodes and pass through the piezoelectric body substrate in the thickness direction when the piezoelectric body substrate is seen from a thickness direction;
an input and output circuit that independently inputs and outputs a signal from and to each of the columnar electrodes; and
a control unit that controls the piezoelectric body.

10. The electronic apparatus according to claim 9,
wherein the control unit performs an ultrasonic wave transmission process of driving the piezoelectric body to transmit ultrasonic waves and an ultrasonic wave reception process of receiving ultrasonic waves by the piezoelectric body, and measures an object to be measured, on the basis of transmission and reception timings of the ultrasonic waves.

* * * * *